(12) United States Patent
Ford

(10) Patent No.: US 10,545,106 B2
(45) Date of Patent: Jan. 28, 2020

(54) COMBUSTION TUBE

(71) Applicant: Leco Corporation, St. Joseph, MI (US)

(72) Inventor: Gordon C. Ford, St. Joseph, MI (US)

(73) Assignee: Leco Corporation, St. Joseph, MI (US)

(*) Notice: Subject to any disclaimer, the term of this patent is extended or adjusted under 35 U.S.C. 154(b) by 0 days.

(21) Appl. No.: 14/661,515

(22) Filed: Mar. 18, 2015

(65) Prior Publication Data

US 2015/0268181 A1 Sep. 24, 2015

Related U.S. Application Data

(60) Provisional application No. 61/968,795, filed on Mar. 21, 2014.

(51) Int. Cl.
*G01N 31/12* (2006.01)
*G01N 25/24* (2006.01)

(52) U.S. Cl.
CPC .................. *G01N 25/24* (2013.01)

(58) Field of Classification Search
CPC .......................... G01N 31/12; G01N 33/225
USPC ........................................ 422/78, 50
See application file for complete search history.

(56) References Cited

U.S. PATENT DOCUMENTS

| | | | |
|---|---|---|---|
| 2,809,100 A | 10/1957 | Krasl | |
| 3,923,464 A | 12/1975 | Sitek et al. | |
| 4,234,541 A | 11/1980 | Bredeweg et al. | |
| 4,699,759 A * | 10/1987 | Feild, Jr. | G21C 3/334 376/441 |
| 5,573,062 A * | 11/1996 | Ooba | B21C 37/16 138/38 |
| 8,377,397 B2 | 2/2013 | Ford | |
| D678,791 S | 3/2013 | Ford | |
| 8,884,193 B2 | 11/2014 | Ford | |
| 2005/0161209 A1* | 7/2005 | Havard, Jr. | F24H 3/087 165/177 |
| 2012/0225000 A1* | 9/2012 | Ford | G01N 31/12 422/549 |

* cited by examiner

*Primary Examiner* — Natalia Levkovich
(74) *Attorney, Agent, or Firm* — Price Heneveld LLP

(57) ABSTRACT

A combustion tube comprises a generally cylindrical body with an outwardly extending tube stop spaced from one end of the combustion tube for engaging a combustion tube mounting assembly and fixing the tube in a precise position. Near the opposite end of the tube is an enlarged opening for receiving an upper seal assembly of a combustion furnace with the outer annular shoulder of the upper end of the tube having a rolled edge to facilitate the insertion of the tube through the seal in the upper seal assembly of the furnace. The combustion tube is made of quartz glass to withstand the temperatures encountered in the furnace. The combustion tube is specifically designed and adapted to be precisely positioned in an induction furnace with an easy tube removal system for the furnace.

9 Claims, 9 Drawing Sheets

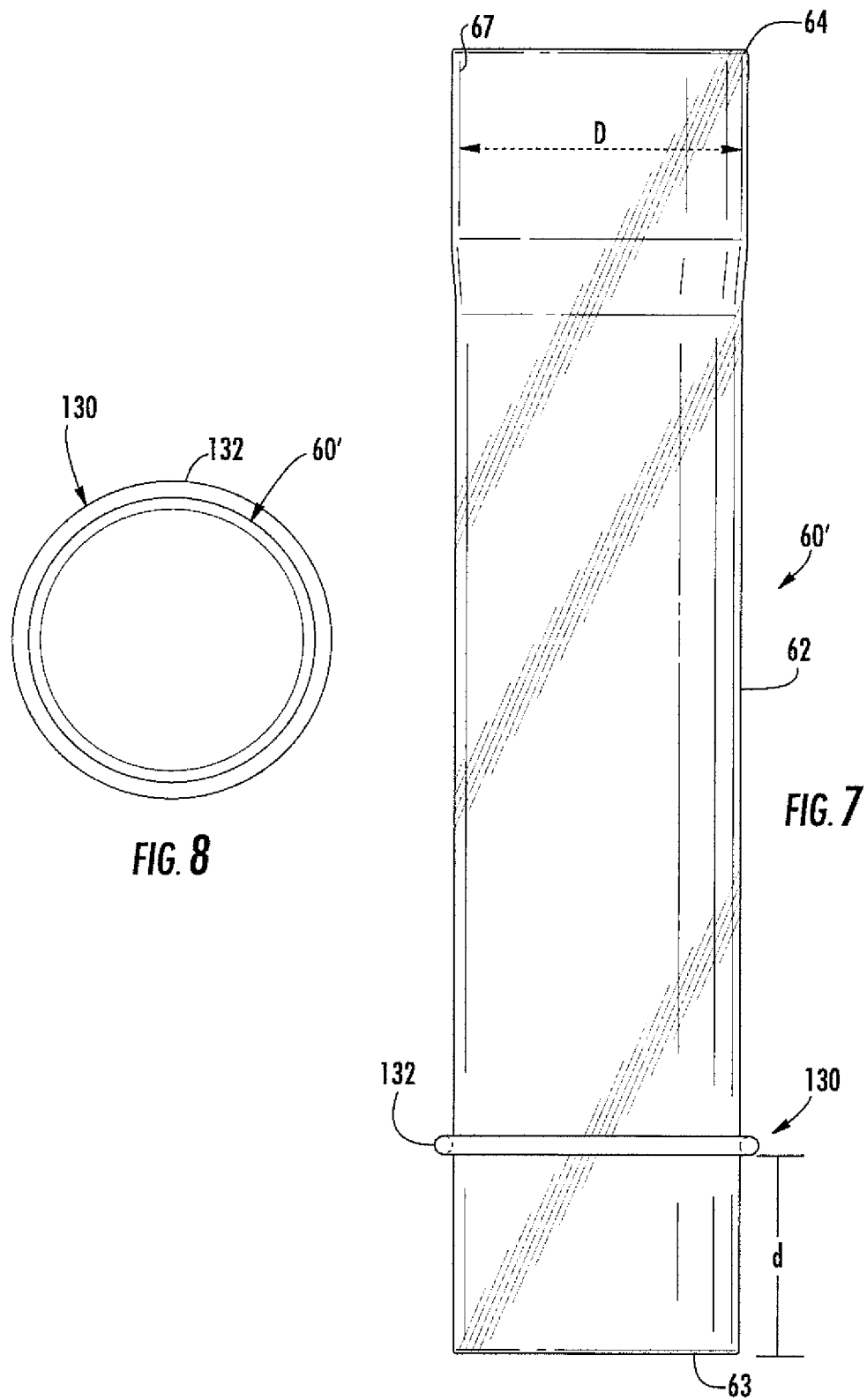

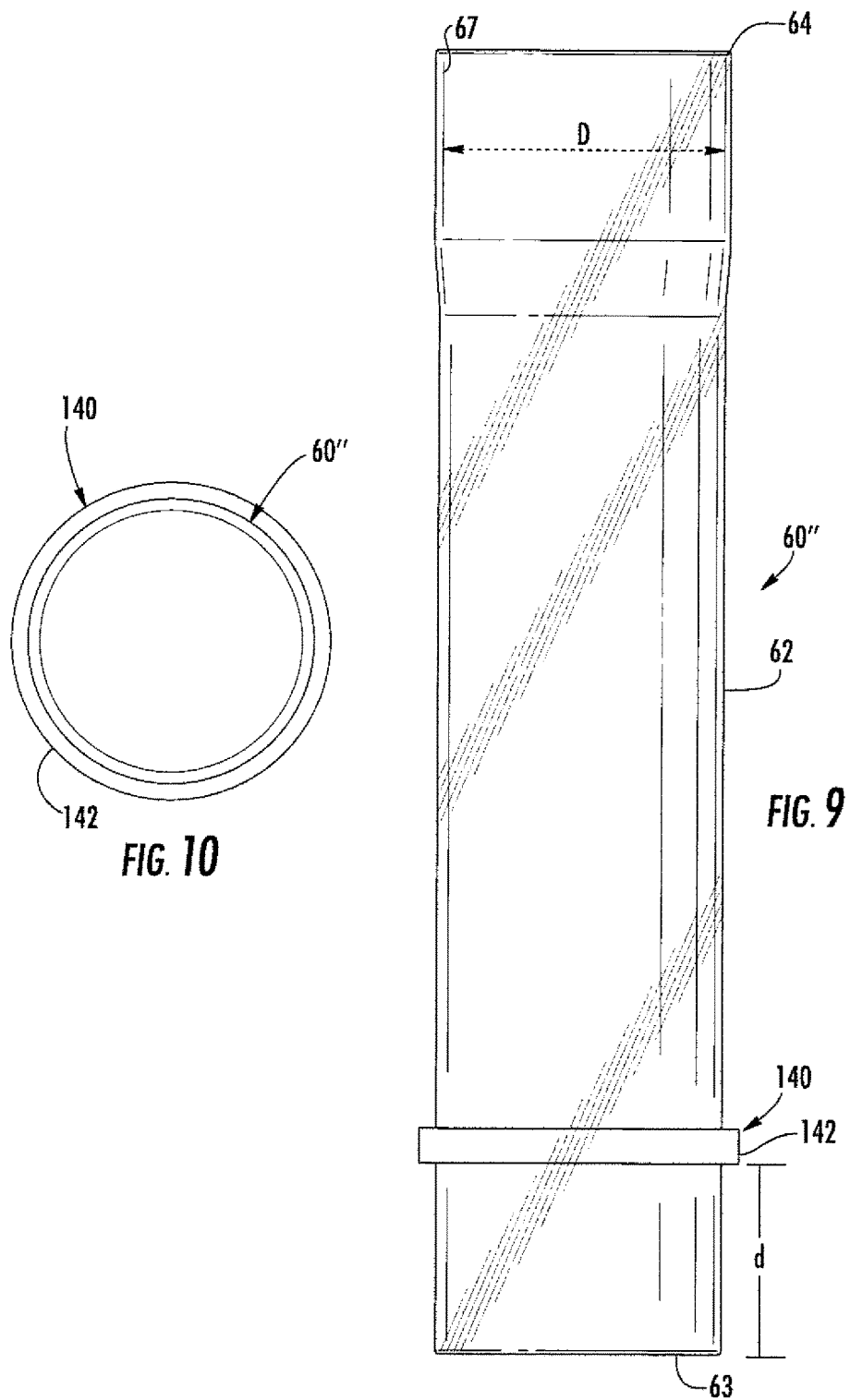

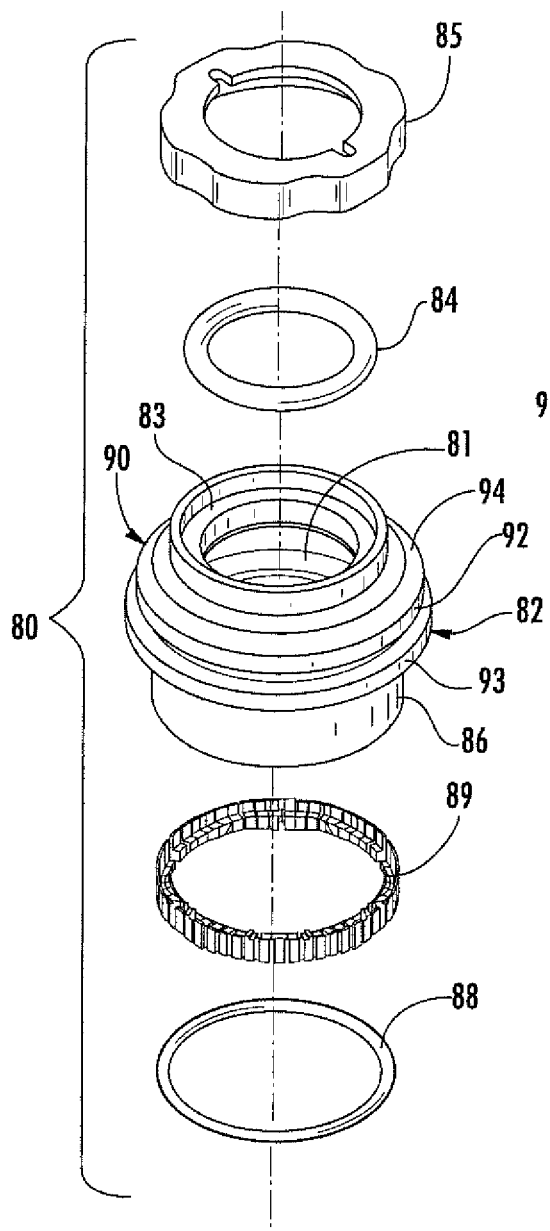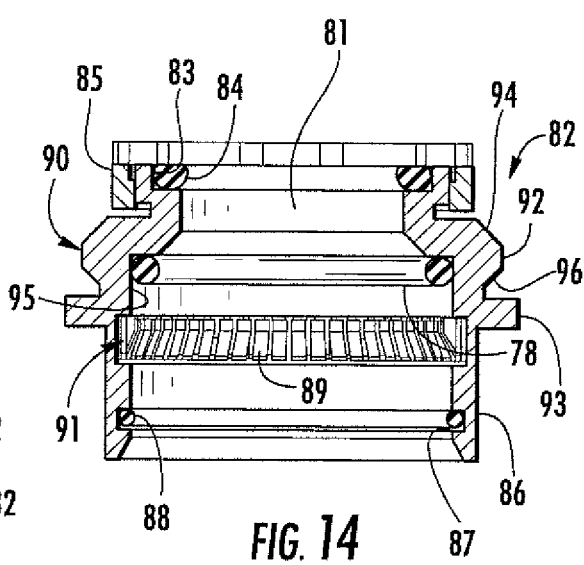
FIG. 14
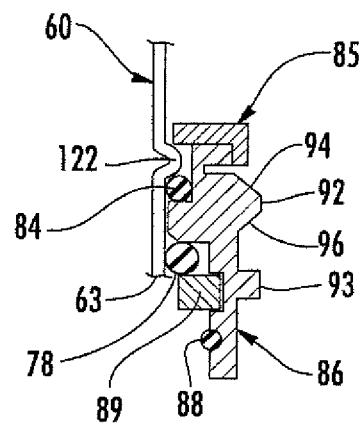
FIG. 12
FIG. 13

COMBUSTION TUBE

CROSS-REFERENCE TO RELATED APPLICATIONS

This application claims priority under 35 U.S.C. § 119(e) and the benefit of U.S. Provisional Application No. 61/968,795 entitled COMBUSTION TUBE, filed on Mar. 21, 2014, by Gordon C. Ford, the entire disclosure of which is incorporated herein by reference.

BACKGROUND OF THE INVENTION

The present invention relates to a combustion tube for an induction furnace employed in an analytical instrument.

Quartz combustion tubes have been used in connection with combustion furnaces for many years for enclosing a sample for the analysis of elements, such as carbon or sulfur. One example of a commercially available analyzer is Model No. CS744, available from Leco Corporation of St. Joseph, Michigan. Such an analyzer uses a unique quartz combustion tube which is easily removable as disclosed in U.S. Pat. Nos. 8,884,193; 8,377,397 and D678,791. These tubes are typically used to maintain a pressurized oxygen-rich environment for the combustion of a sample in a ceramic crucible held within an induction coil surrounding the combustion tube. U.S. Pat. Nos. 2,809,100, 3,923,464, and 4,234,541 are also examples of systems employing quartz combustion tubes. The disclosures of these patents are incorporated herein by reference.

During the combustion process, byproducts of combustion frequently cause deposits on the combustion tube. The quartz tube must be cleaned and eventually replaced to maintain the accuracy of sample results. The mounting of a combustion tube in existing furnaces equipped with an auto cleaner is both time consuming and cumbersome, requiring that fluid fittings and electrical connections be removed and the auto-cleaner device removed from the combustion tube area of the furnace. The combustion tube is removed from the top of the furnace housing once the disassembly has been completed. Once a new combustion tube has been installed, the furnace has to be reassembled, frequently including the connection of fluid couplings which can lead to leaks in the system if not properly accomplished. Thus, the maintenance, removal and replacement of combustion tubes in existing furnaces is difficult, time consuming, and leads to downtime for the operation of an analyzer.

This invention relates to improved combustion tube designs for use in an analytical combustion furnace which can be readily accessed without disconnecting fluid fittings, auto-cleaners, or the like from the furnace assembly.

SUMMARY OF THE INVENTION

The system of the present invention accomplishes this goal by providing an improved combustion tube which cooperates with a mounting system for the combustion tube. The combustion tube is removably installed through an aperture in the floor of a furnace housing and can be manually or automatically unlocked from the floor of the furnace housing by a cam-locking mechanism for positioning the combustion tube in an open area of the furnace below the furnace housing for easy removal and replacement.

In a preferred embodiment, a combustion tube includes a generally cylindrical body with a tube stop spaced from one end to locate the combustion tube in precise alignment in an induction furnace with which the tube is employed. Several different tube stops are disclosed. They include a plurality of radially outwardly extending dimples, radially outwardly extending arcuate projections, a ring or partial sections of a ring coupled to the outer surface of the cylindrical body, or pins extending radially outwardly.

These and other features, objects and advantages of the present invention will become apparent upon reading the following description thereof together with reference to the accompanying drawings.

BRIEF DESCRIPTION OF THE DRAWINGS

FIG. 7 is a front elevational view of another embodiment of the combustion tube of this invention;

FIG. 8 is a bottom plan view of the combustion tube of FIG. 7;

FIG. 9 is a front elevational view of another embodiment of the combustion tube of this invention;

FIG. 10 is a bottom plan view of the combustion tube of FIG. 9;

FIG. 12 is an enlarged fragmentary cross-sectional view of the interface between the combustion tube of FIGS. 5 and 6 and the lower seal assembly, although a similar interface exists with the combustion tubes of FIGS. 7-10;

FIG. 13 is an exploded perspective view of the lower seal assembly; and

FIG. 14 is an enlarged cross-sectional view of the lower seal assembly.

DETAILED DESCRIPTION OF THE PREFERRED EMBODIMENT

Figure 1:
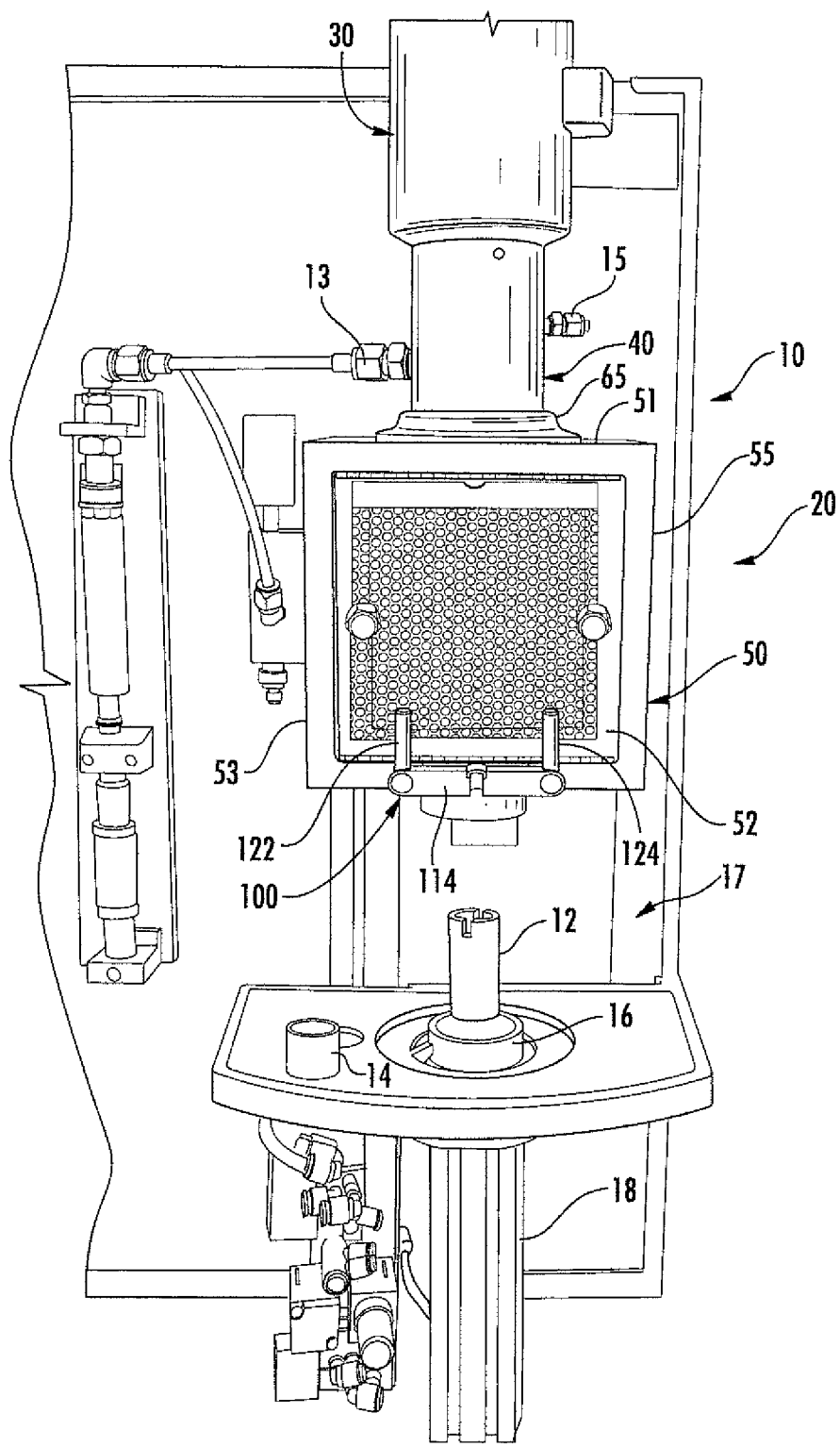
FIG. 1 is a fragmentary front perspective view of a combustion furnace embodying the present invention.
Figure 2:
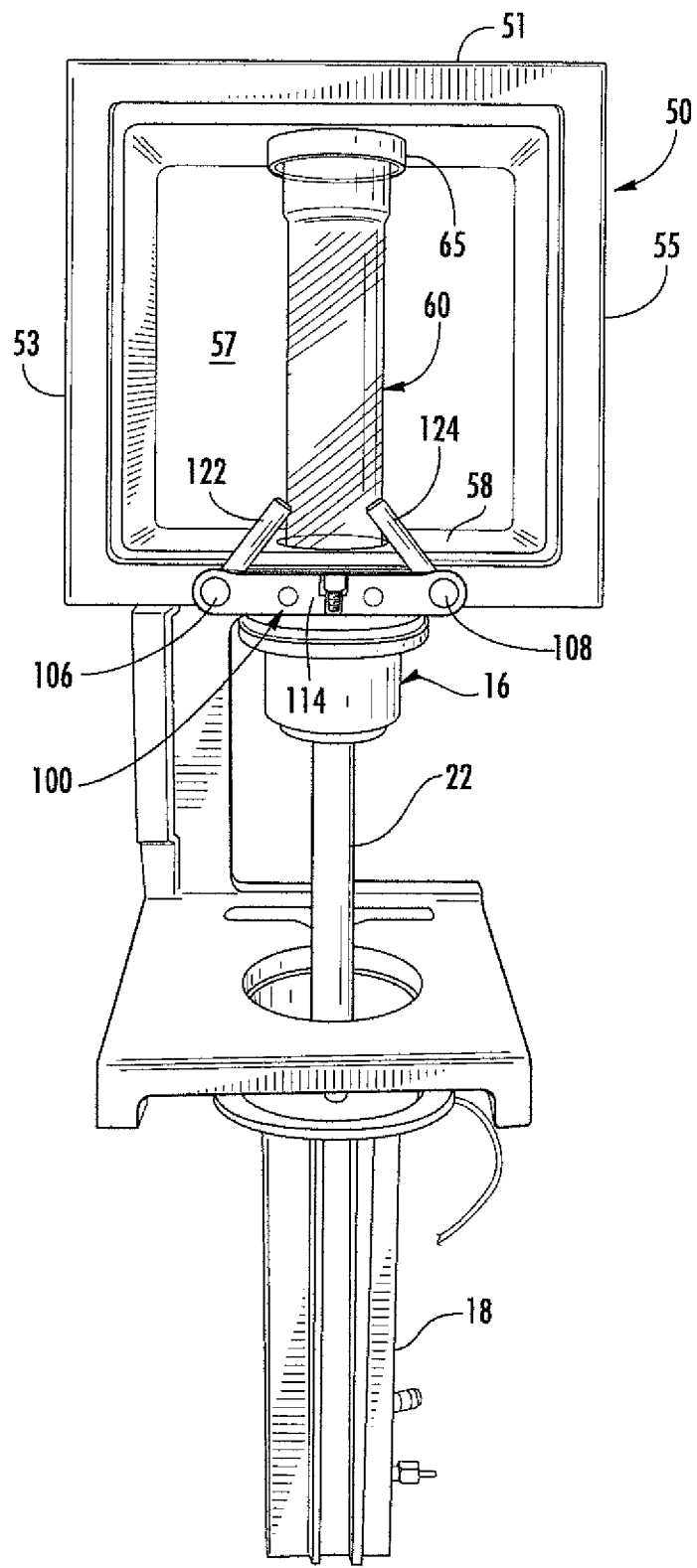
FIG. 2 is a front perspective view of the furnace housing with the cover removed showing the combustion tube and locking mechanism for the tube, shown in an unlocked position.
Figure 3:
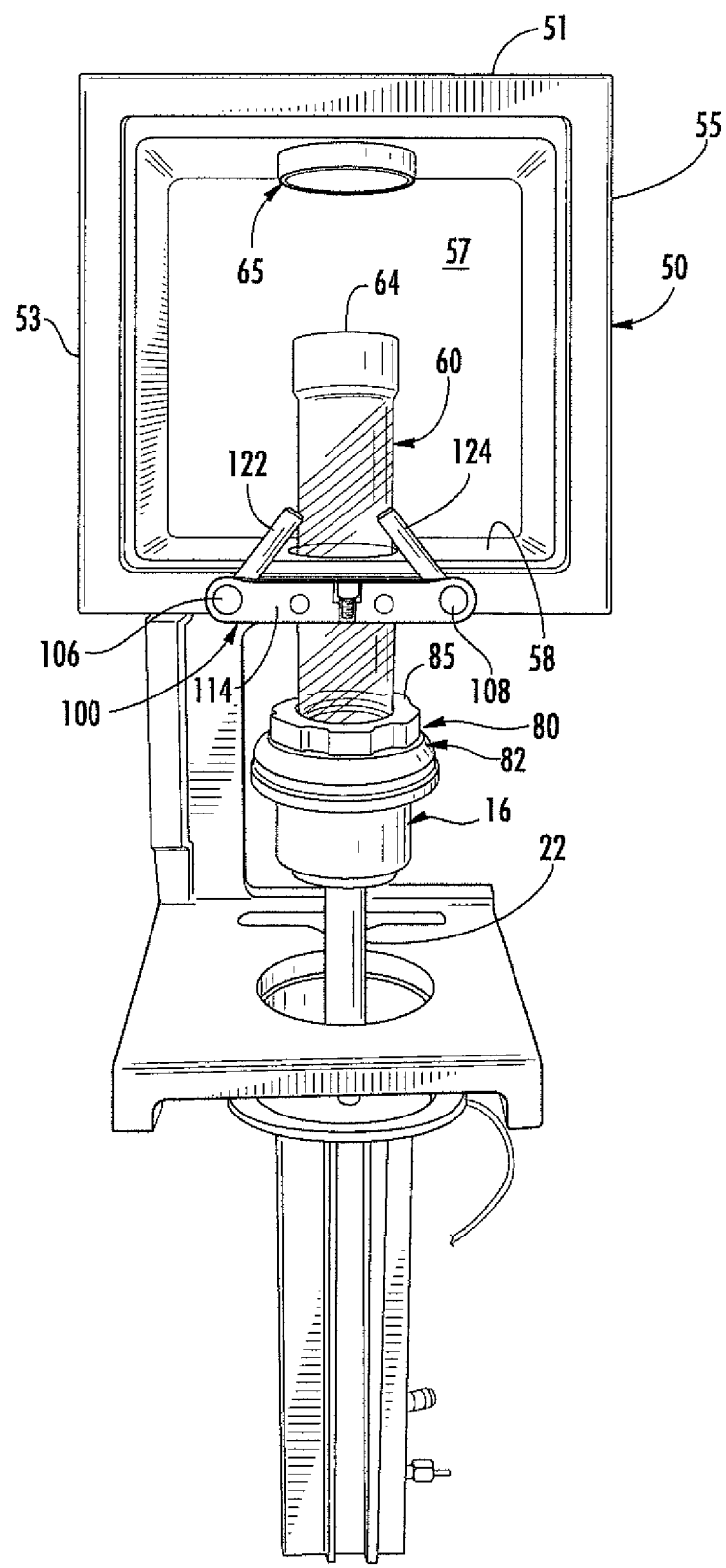
FIG. 3 is a front perspective view of the furnace shown in FIG. 2, showing the lowering and raising of the combustion tube through an aperture in the furnace housing floor.
Figure 4:
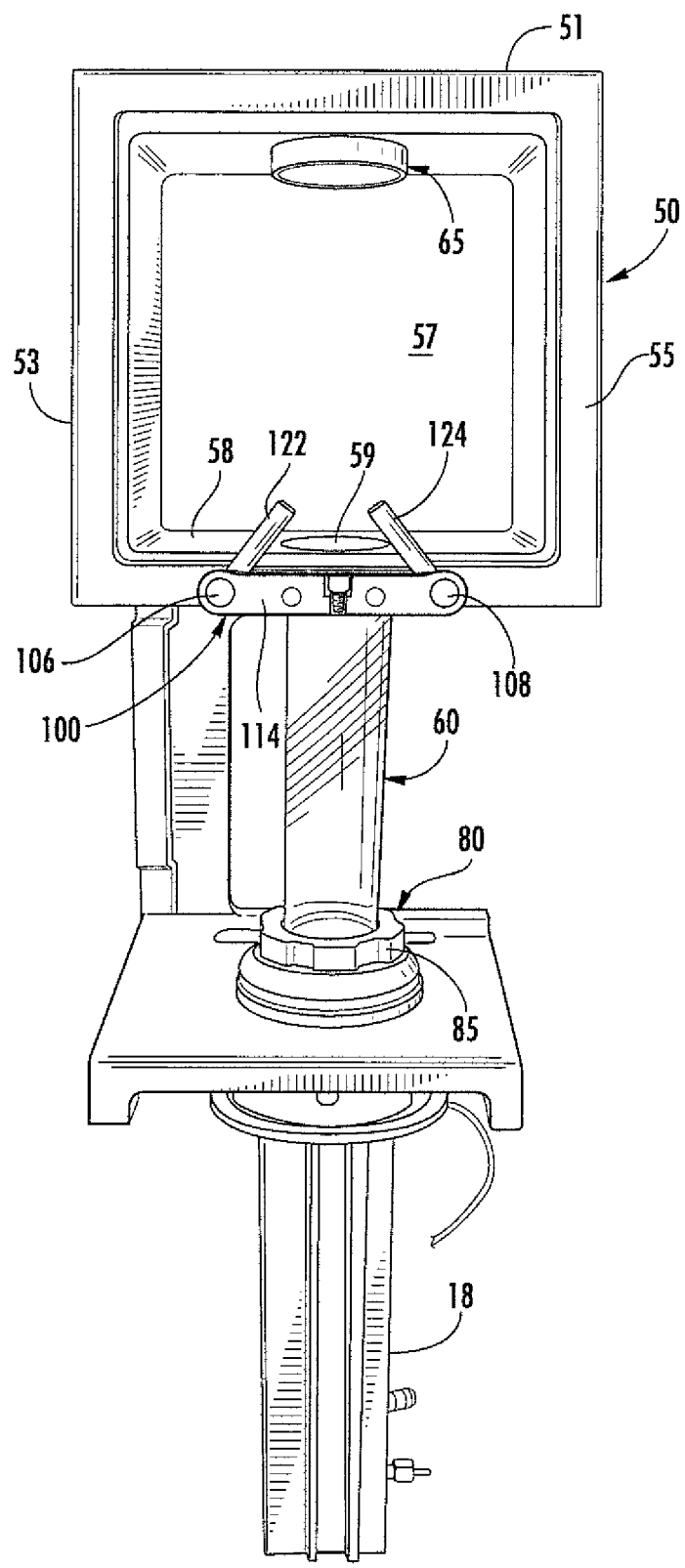
FIG. 4 is a front perspective view of the furnace shown in FIG. 3, showing the combustion tube lowered from the furnace housing in a position for removal/replacement.

Referring initially to FIG. 1, there is shown an analyzer 10 which includes an induction furnace assembly 20, including the auto cleaning mechanism 30 described in detail in U.S. patent application Ser. No. 13/198,746, filed Aug. 5, 2011, entitled COMBUSTION FURNACE AUTO CLEANER, the disclosure of which is incorporated herein by reference. The analyzer components themselves can be similar to those employed in a carbon sulfur analyzer, Model No. CS744, available from Leco Corporation of St. Joseph, Mich. The analyzer 10 is shown in FIG. 1 with the cover shrouds removed to expose the components of the induction furnace, which are also shown in FIGS. 2-4. The detachable auto cleaner assembly 30 is removably mounted by a bayonet connection to a heated filter assembly 40, which is sealably secured at 65 to the top wall 51 of combustion housing 50. Housing 50 additionally includes side walls 53 and 55, an interface back wall 57, and floor 58. The housing 50 is mounted to structural base 17 of the analyzer 10, which includes housing 50. The front of furnace housing 50 is enclosed by a quickly removable door 52, which, when removed as seen in FIG. 2, exposes the combustion tubes of the present invention (FIGS. 5-10). An induction coil (not shown) conventionally surrounds the combustion tubes to heat an analytical specimen held in a ceramic crucible 14 (FIG. 1) when introduced into the hot zone of one of the combustion tube 60, for example, by positioning the crucible on a vertically movable pedestal 12. Each of the combustion tubes when installed are sealably coupled to the lower end of filter assembly 40 by an upper seal assembly 65. The pedestal 12 (FIG. 1) for holding a sample-holding crucible 14 is positioned on a cup-shaped lower seal assembly 16 and is raised and lowered into combustion tube 60 by means of a pneumatic cylinder 18 and cylinder rod 22 (FIGS. 2 and 3) coupled to assembly 16. In the position shown in FIG. 1, the cylinder rod 22 is in a lowered retracted position within cylinder 18.

A combustion tube base assembly 80 (FIGS. 3, 4, and 11,) sealably couples the lower end 63 of each of the combustion tubes, such as tube 60, to the pedestal's lower seal assembly 16 such that, during combustion of a sample, oxygen flows upwardly through a gas inlet in assembly 16 to sweep byproducts of combustion into gas outlet 13 (FIG. 1) for analysis. Oxygen is also supplied to the upper end of combustion tube 60 by an oxygen inlet 15 and suitable passageways to an inlet lance to direct oxygen into crucible 14 during combustion. Housing 50 includes cam-actuated locking assembly 100 (FIGS. 2-4) which cooperates with base assembly 80 to allow the combustion tubes to be easily withdrawn through aperture 59 (FIG. 4) in the floor 58 of combustion housing 50. Assembly 100 includes arms 122, 124 on pivoted cams 106, 108 mounted to housing 50 by a mounting plate 114, as described in detail in U.S. Pat. No. 8,884,193 entitled EASILY REMOVABLE COMBUSTION TUBE, the disclosure of which is incorporated herein by reference.

Figure 5:
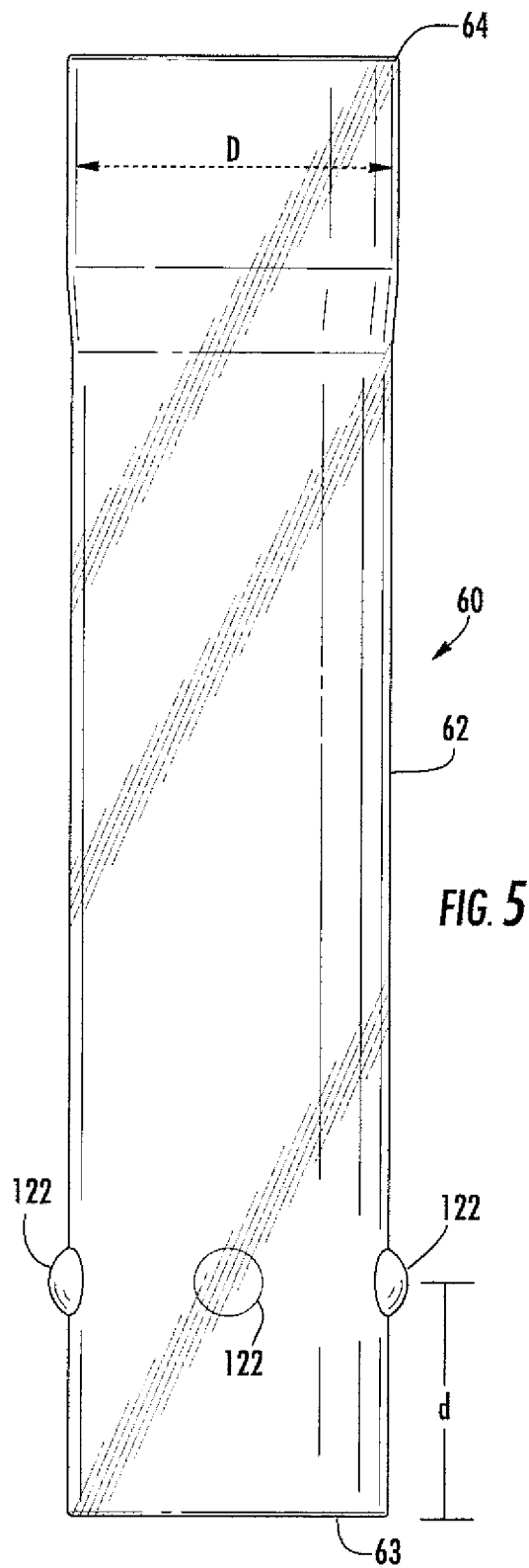
FIG. 5 is a front elevational view of one embodiment of the combustion tube of this invention.

Referring to FIGS. 5-10, there is shown three different combustion tubes 60, each of which has a generally cylindrical body 62, including a first or lower end 63 and a second or upper end 64. Spaced from the lower end a predetermined distance "d" (shown in FIG. 6) is one of a variety of tube stops 120 described below. The opposite or top end 64 of the tube is enlarged to provide a somewhat larger diameter "D", as seen in FIGS. 5, 7, and 9, such that the outer surface of the upper end 64 of tube 60 mates with an internal O-ring in the upper seal assembly 65 (FIGS. 2-4) of the furnace 20. The annular upper end 64 of the combustion tube 60 has a rolled edge which provides a rounded interface between the upper end of tube 60 as it engages the seal of the upper seal assembly 65, as illustrated in FIG. 2.

Figure 6:
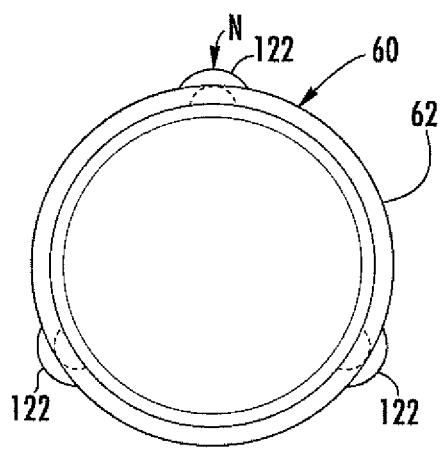
FIG. 6 is a bottom plan view of the combustion tube of FIG. 5.

As seen in FIGS. 5 and 6, one of the tube stops 120 takes the form of a plurality of outwardly projecting dimples 122 which are, in the embodiments shown in FIGS. 5 and 6, spaced at approximately 120° intervals. There can be "n" number of equally spaced dimples where "n" is an integer from 2 to 15, for example. The dimples 122 tend to extend outwardly from the outer diameter of tube body 62 a distance of about 0.065 inches, which is a distance sufficient to interface with the base assembly 80 and cap 85 to index and mount the combustion tube to the base assembly 80. The distance "d" of the center of dimples 100 to the bottom edge 63 of the combustion tube 60 is important in indexing the tube within the furnace for a tube having an overall length of about 6.12 inches and the inner diameter "D" near the top of about 1.28 inches. The distance was about 0.83 inches to provide sealed engagement of the lower end 63 of the combustion tube within seal 84, as illustrated in FIG. 12.

In another embodiment, instead of a plurality of equally arcuately spaced dimples 122 which are longitudinally aligned along the combustion tube 60, a ring 132 or arcuate sections of a ring, such as a quartz rod (FIGS. 7 and 8), can be fused and/or formed during manufacturing around the cylindrical walled combustion tube 60' to provide a tube stop 130. The diameter of the glass rod 132, typically made of quartz and fused to the body 62 of the combustion tube 60', is equivalent to the diameter of the outwardly projecting distance of the dimples 122 shown in FIGS. 5 and 6, namely, about 0.065 inches. The dimples could be replaced by stainless steel or ceramic pins which are integrally formed in the body of the combustion tube and located in vertical alignment around the periphery of the tube like the dimples, such pins can vary in number as long as they provide the desired alignment function of the tube in the furnace. For purpose of illustration, the pins and dimples should be considered as illustrated in FIGS. 5 and 6.

In yet another embodiment of the invention shown in FIGS. 9 and 10, a tube stop 140 is shown comprising a separate metal or glass sleeve 142 having an inner diameter approximately corresponding to the outer diameter of the body 62 of combustion tube 60" of about 1.48 inches. The metal or glass sleeve 142 forming the tube stop can be fused onto the body 62 of combustion tube 60", cemented with a suitable refractory cement or otherwise coupled to the tube in a permanent fashion which withstands the temperatures of combustion to which the tube is exposed in the furnace during use.

The upper end 64 of each of the combustion tubes engage the upper seal assembly 65, which includes an internal O-ring seal on a collar that engages the outer cylindrical surface of the mouth 67 of the combustion tube. The furnace 20 also includes a base assembly 80, shown in detail in FIGS. 12-14, which receives the lower end 63 of combustion tubes 60, 60', 60" with the tube stops, in whatever form they take, indexing the position of the tube with respect to the lower base assembly 80.

Figure 11:
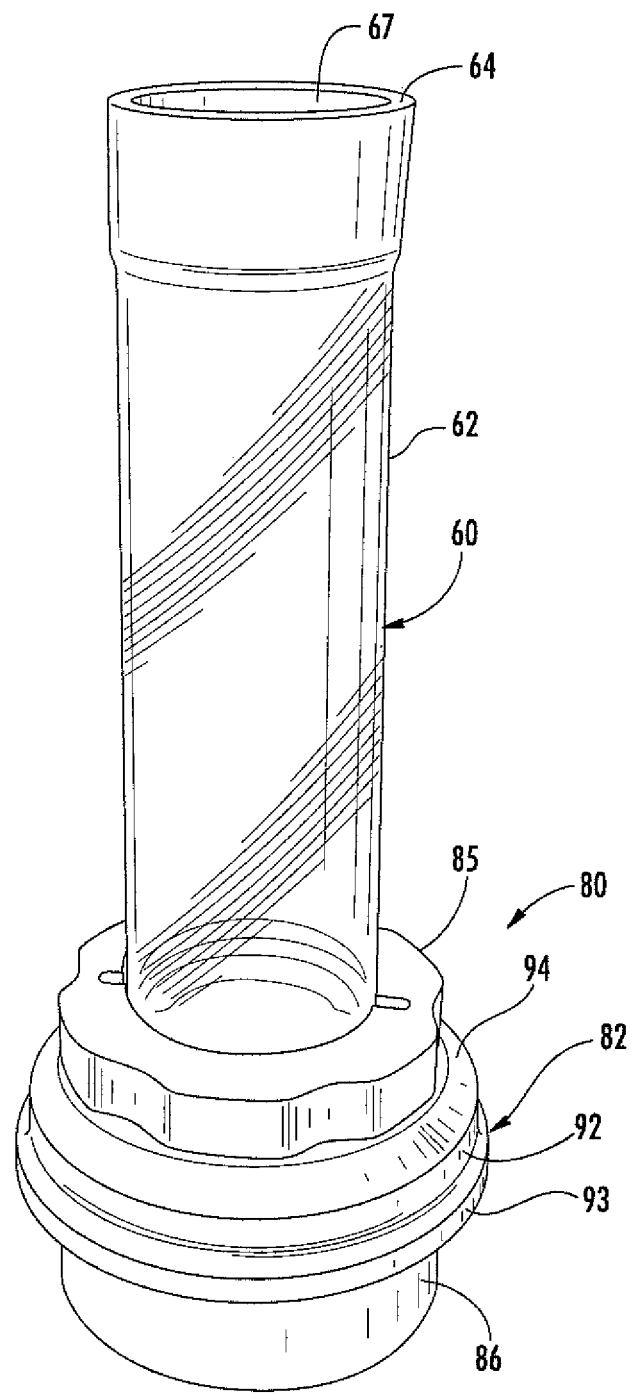
FIG. 11 is an enlarged perspective view of any one of the combustion tubes of FIGS. 5-10, shown mounted within the lower seal assembly.

The base assembly 80 has a generally cylindrical collar 82 with a central aperture 81 therein for receiving a combustion tube 60, as seen in FIG. 11. As seen in FIG. 13, near the upper edge of collar 82 is an annular recess 83 for receiving an O-ring seal 84. A locking cap 85 is threaded onto collar 82 and compresses the O-ring seal once the combustion tube has been inserted therein for sealably holding the combustion tube within the collar 82. Cap 85 engages stop 122 of combustion tube 60 compressing seal 84 (FIG. 12) and vertically aligns the combustion tube 60 with respect to the base assembly 80 and ultimately the furnace 20, as seen in FIGS. 2-4 . Collar 82 includes a lower cylindrical sleeve 86 having internal annular recess 87 for receiving a second O-ring 88 for sealing the base assembly 80 onto the lower seal assembly 16 of the furnace. Further, the assembly 80 includes a metal RFI shield 89 and a third sealing O-ring 78 (FIGS. 12-14) positioned within an annular recess 95 of collar 82 above shield 89.

As seen in FIGS. 12-14, collar 82 includes a cam 90 which has an outer annular vertical surface 92, an upper chamfered surface 94 chamfered upwardly and inwardly at an angle of about 45° from the vertically extending annular surface 92 and a lowered chamfered surface 96 inwardly and downwardly beveled at an angle of about 45° from surface 92. The two surfaces thus form an angle of about 90° between them to fit within a 90° slot (not shown) in the cams 106 and 108. Collar 82 also includes an annular flange 93 having a diameter greater than aperture 59 in furnace housing floor 58 to engage the undersurface of floor 58 when the combustion tube is in an installed locked position as seen in FIG. 3. The cam 90 so-defined interengages with cam pins 106, 108 of cam-actuated assembly 100 for locking and unlocking the combined combustion tube 60 and base assembly 80 as described in greater detail the above identified '193 patent.

The combustion tubes 60, 60', 60" are made of quartz glass to withstand the temperatures of combustion, which can reach 3000° C. The combustion tubes have an overall length (i.e., height) of about 6.12 inches, with the inner diameter D near the top having a diameter of about 1.28 inches. The outer diameter of the cylindrical body 62 of the tubes is about 1.48 inches, while the outer stops have an outer diameter of about 1.58 inches. The radius of curvature of the dimples 122, for example, are about 0.010 inches. The vertical height of dimples 122 was about 0.157 inches. Thus, the stops 120, 130, and 140 project outwardly from the outer surface 62 of combustion tube 60 about 0.065 inches, a distance sufficient to interface with the base assembly 80 and cap 85 to index and mount the combustion tubes to the base assembly 80. The distance from these stops to the bottom edge 63 of tube 60 was about 0.83 inches to provide a distance sufficient for the sealed engagement of the lower end 63 of the combustion tube with seal 84, as illustrated in FIG. 12. The wall thickness of the combustion tubes was, in one preferred embodiment, about 2 mm. Although these dimensions are illustrative of the preferred embodiment of the invention, other sized furnaces may incorporate combustion tubes with proportionally larger or smaller dimensions, as long as the unique mounting and sealing arrangement is provided for the combustion tubes. The important feature is that a stop collar is provided in spaced relationship to the lower edge of the combustion tube to allow its indexable and sealable mounting to a base assembly for easy removal, particularly in a furnace having an easily removable combustion tube design.

FIG. 3 illustrates the assembly of a combustion tube 60 to the lower seal assembly 16, which includes an upper ring 85 threadably mounted to the collar 82 of the base assembly. As seen in FIGS. 3, 11 and 12, when combustion tube 60 is inserted into the base assembly 80, the stops, such as stop 122, engage the seal 84 at the cylindrical bottom edge of upper ring 85 to precisely position the combustion tube with respect to the base assembly 80. Engaging the bottom of upper ring 85 assures positive removal of the combined assembly 80 and tube 60 when disengaged from furnace 20. This allows assembly 80 to cooperate with the raising and lowering mechanism, including the piston rod 22, lower seal assembly 16, and pedestal 12 (FIGS. 1 and 3) to precisely position the combustion tube 60 within the analytical furnace 20. Thus, with the improved combustion tubes of the present invention, an indexing stop is provided to precisely mount and position the combustion tube in the furnace, particularly when used in connection with an easily removable combustion tube mechanism.

It will become apparent to those skilled in the art that various modifications to the preferred embodiment of the invention as described herein can be made without departing from the spirit or scope of the invention as defined by the appended claims.

The invention claimed is:
1. An analytical furnace comprising:
   a combustion tube comprising a generally cylindrical body made of quartz glass and having a tube stop spaced from a first end of said body, wherein said tube stop comprises a plurality of spaced-apart extensions formed radially outwardly from an outer surface of said body, said extensions angularly spaced-apart from each other along a perimeter of said tube, each extension positioned at a constant distance d from said one end of said body;
   a combustion housing including an induction coil for heating the combustion tube, the combustion housing having a floor with an aperture from which the combustion tube is configured to be inserted in a vertical position into the combustion housing from below the floor; and
   a base assembly having a central opening for receiving a lower end of the combustion tube, wherein the central opening is below and in registration with the aperture in the floor of the combustion housing, wherein the tube stop engages the base assembly to position the combustion tube in a predetermined position with respect to the base assembly and the combustion housing when the combustion tube is in a fully inserted position in the combustion housing whereby the base assembly is moved into engagement with the floor of the combustion housing.

2. The analytical furnace as defined in claim 1 wherein said extensions comprise at least three dimples formed radially outwardly from said body.

3. The analytical furnace as defined in claim 1 wherein said extensions are made of one of metal and ceramic material.

4. The analytical furnace as defined in claim 1 wherein the body of the combustion tube includes a second end opposite the first end, the second end has an outer annular shoulder having a rolled edge to facilitate the insertion of the second end through a seal in an upper seal assembly of the furnace.

5. An induction furnace comprising:
   a combustion tube comprising:
      a generally cylindrical body made of quartz glass; and
      a tube stop comprising a plurality of spaced-apart projections on said body, each projection located in predetermined constant spaced relationship of about 0.8 inches from one end of said body and extending outwardly from said body about 0.06 inches, said projections angularly spaced-apart from each other along a perimeter of said body; and
   a combustion housing including an induction coil for heating the combustion tube, the combustion housing having a floor with an aperture from which the combustion tube is configured to be inserted in a vertical position into the combustion housing from below the floor; and
   a base assembly having a central opening for receiving a lower end of the combustion tube, wherein the central opening is below and in registration with the aperture in the floor of the combustion housing, wherein the tube stop engages the base assembly to position the combustion tube in a predetermined position with respect to the base assembly and the combustion housing when the combustion tube is in a fully inserted position in the combustion housing whereby the base assembly is moved into engagement with the floor of the combustion housing.

6. The induction furnace as defined in claim 5 wherein said projections are formed radially outwardly from said body.

7. The induction furnace as defined in claim 6 wherein said tube stop comprises at least three projections formed radially outwardly from said body.

8. The analytical furnace as defined in claim 2 wherein said projections are spaced-apart at 120° intervals.

9. The induction furnace as defined in claim 7 wherein said projections are spaced-apart at 120° intervals.

\* \* \* \* \*